United States Patent
Burnard et al.

(10) Patent No.: US 11,202,859 B2
(45) Date of Patent: Dec. 21, 2021

(54) CASSETTE WITH FREE FLOW PREVENTION FOR INFUSION PUMP

(71) Applicant: B. BRAUN MEDICAL INC., Bethlehem, PA (US)

(72) Inventors: Edwin Leighton Burnard, Fogelsville, PA (US); Anthony Dibella, Franklin, MA (US); Dan Smith, Portsmouth, RI (US); John Ristuccia, Easton, MD (US)

(73) Assignee: B Braun Medical Inc., Bethlehem, PA (US)

( * ) Notice: Subject to any disclaimer, the term of this patent is extended or adjusted under 35 U.S.C. 154(b) by 177 days.

(21) Appl. No.: 16/689,841

(22) Filed: Nov. 20, 2019

(65) Prior Publication Data
US 2021/0146044 A1     May 20, 2021

(51) Int. Cl.
*A61M 5/168*     (2006.01)
*A61M 5/142*     (2006.01)

(52) U.S. Cl.
CPC .... *A61M 5/16813* (2013.01); *A61M 5/14232* (2013.01); *A61M 2205/128* (2013.01); *A61M 2205/505* (2013.01)

(58) Field of Classification Search
CPC .............. A61M 5/14228; A61M 5/142; A61M 2005/14533; A61M 39/281; A61M 5/14232
See application file for complete search history.

(56) References Cited

U.S. PATENT DOCUMENTS

| | | | | |
|---|---|---|---|---|
| 4,416,595 A | * | 11/1983 | Cromie | A61M 5/142 128/DIG. 12 |
| 4,585,441 A | * | 4/1986 | Archibald | A61M 5/36 128/DIG. 12 |
| 4,637,817 A | * | 1/1987 | Archibald | A61M 5/16827 604/81 |
| 4,689,043 A | * | 8/1987 | Bisha | A61M 5/142 128/DIG. 13 |
| 5,017,192 A | * | 5/1991 | Dodge | A61M 39/287 251/7 |
| 5,290,239 A | * | 3/1994 | Classey | A61M 39/287 128/DIG. 12 |
| 5,445,613 A | * | 8/1995 | Orth | A61M 39/281 251/14 |
| 5,478,211 A | * | 12/1995 | Dominiak | A61M 5/142 417/234 |

(Continued)

*Primary Examiner* — Scott J Medway

(57) ABSTRACT

A cassette with free flow prevention for use with an ambulatory pump. The cassette includes a free flow prevention clamp and a housing. The free flow prevention clamp includes a clamping section having a first side and a second side, a first elongate section extending from the first side, and a second elongate section extending from the second side. The housing supports the free flow prevention clamp and defines a channel for receiving a tube. The elongate sections extend parallel to the channel and the clamping section extends across the channel. The free flow prevention clamp is configurable within the housing in an open condition that allows fluid flow through the tube when force is applied to one of the elongate sections and in a closed condition that prevents fluid flow through the tube when the force is removed from the elongate sections.

18 Claims, 5 Drawing Sheets

(56) References Cited

U.S. PATENT DOCUMENTS

| | | | | |
|---|---|---|---|---|
| 5,482,438 A | * | 1/1996 | Anderson | A61M 5/142 417/44.1 |
| 5,658,133 A | * | 8/1997 | Anderson | A61M 5/172 417/63 |
| 5,673,588 A | * | 10/1997 | Raymond | A61M 5/142 200/400 |
| 5,904,668 A | * | 5/1999 | Hyman | A61M 39/08 604/131 |
| 6,629,955 B2 | * | 10/2003 | Morris | A61M 39/287 604/153 |
| 7,611,498 B2 | * | 11/2009 | Hasler | A61M 5/14228 604/131 |
| 8,425,470 B2 | * | 4/2013 | Beck | A61J 15/0026 604/250 |
| 8,932,032 B2 | * | 1/2015 | Orr | A61M 1/14 417/395 |
| 10,850,089 B2 | * | 12/2020 | Grant | A61M 1/3638 |
| 2012/0083737 A1 | * | 4/2012 | Beck | A61M 39/288 604/151 |
| 2014/0219843 A1 | * | 8/2014 | Koyama | F04B 45/08 417/477.3 |
| 2019/0099552 A1 | * | 4/2019 | Zhang | F04B 43/082 |
| 2021/0146044 A1 | * | 5/2021 | Burnard | A61M 5/16813 |

\* cited by examiner

CASSETTE WITH FREE FLOW PREVENTION FOR INFUSION PUMP

FIELD OF THE INVENTION

The present disclosure is related to infusion pumps and, more particularly, to a cassette for use with an infusion pump that includes a free flow prevention device.

BACKGROUND

Infusion pumps deliver controlled doses of fluids such as medications, analgesics, and nutrition to patients. Infusion pumps are particularly well suited to delivering controlled doses of fluids over long periods of time, e.g., several hours or days. While many infusion pumps are designed for bedside use, there are ambulatory versions available. Ambulatory infusion pumps allow a patient to move around while the infusion pump is in use. This is beneficial for patients who would otherwise be confined to a bed, and it can help patients get some light exercise by walking or stretching. This also allows fluids to be delivered while patients are being transferred.

There are two conventional types of infusion pumps, syringe pumps that depress a syringe to deliver fluid from the syringe to a patient, and peristaltic pumps that act on a tube to control the rate of fluid flow through the tube from a bottle or bag of fluid to a patient. A concern with peristaltic pumps is that the force of gravity may cause an unintentional flow of fluid from the bottle or bag of fluid through the tube to the patient, which is commonly referred to as free flow.

SUMMARY

Examples described herein are directed to a cassette for use with an ambulatory pump. The cassette includes a free flow prevention clamp and a housing. The free flow prevention clamp includes a clamping section having a first side and a second side, a first elongate section extending from the first side, and a second elongate section extending from the second side. The housing supports the free flow prevention clamp and defines a channel for receiving a tube. The elongate sections extend parallel to the channel and the clamping section extends across the channel. The free flow prevention clamp is configurable within the housing in an open condition that allows fluid flow through the tube when force is applied to one of the elongate sections and in a closed condition that prevents fluid flow through the tube when the force is removed from the elongate sections.

DRAWINGS

The drawing figures depict multiple views of one or more implementations, by way of example only, not by way of limitations. In the figures, like reference numerals refer to the same or similar elements. The same numeral is used to represent the same or similar element across the multiple views. If multiple elements of the same or similar type are present, a letter may be used to distinguish between the multiple elements. When the multiple elements are referred to collectively or a non-specific one of the multiple elements is being referenced, the letter designation may be dropped.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and circuitry have been described at a relatively high-level, without detail, in order to avoid unnecessarily obscuring aspects of the present teachings.

Figure 1A:
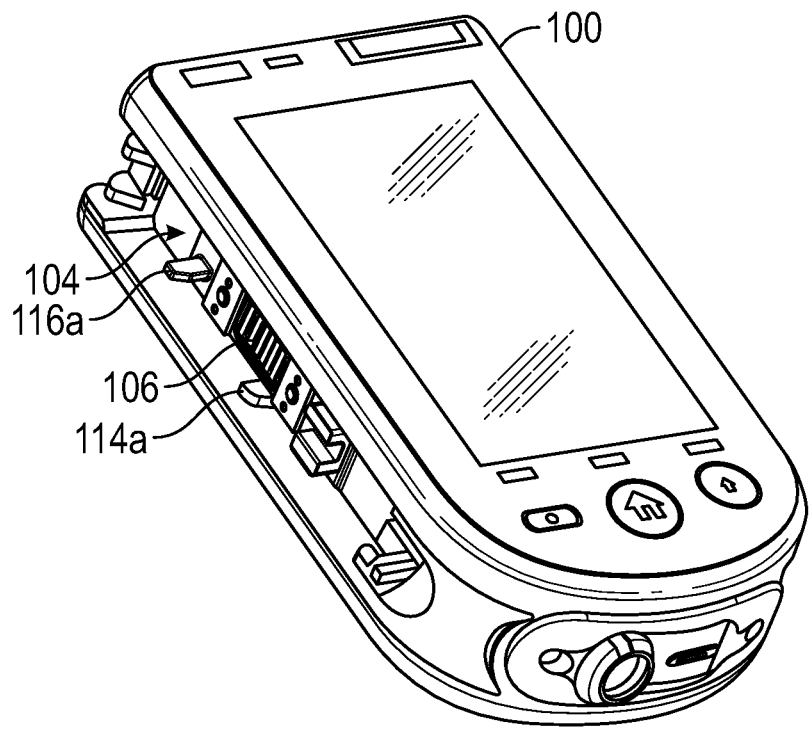
FIG. 1A is a perspective view of an example ambulatory infusion pump.
Figure 1B:
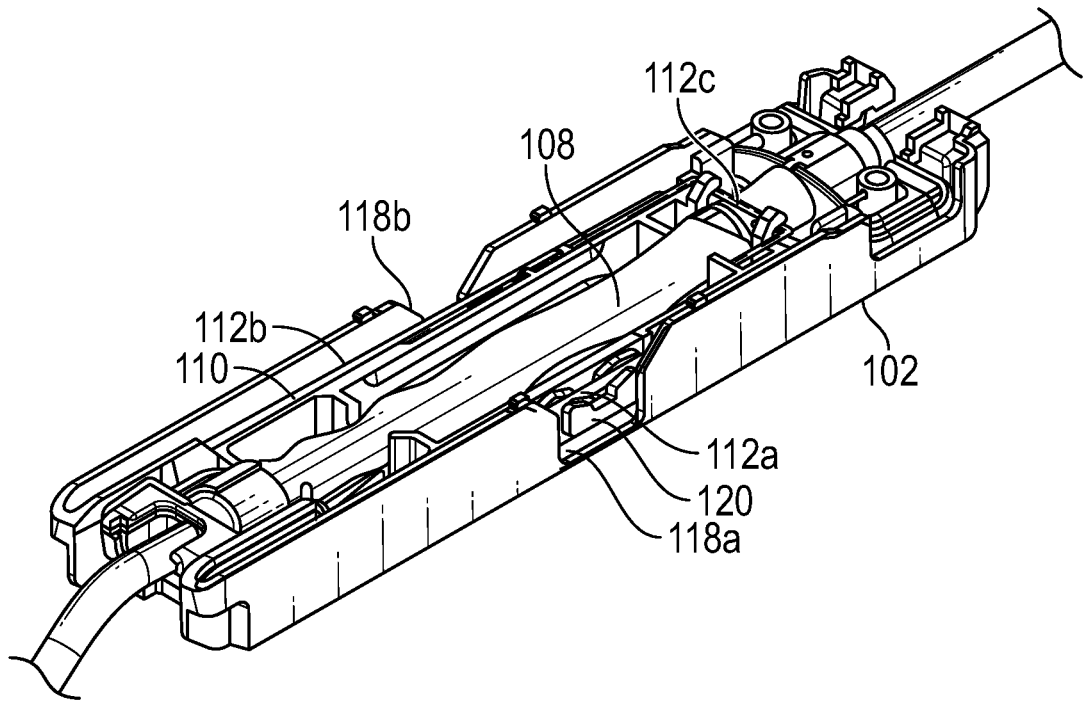
FIG. 1B is a perspective view of an example cassette with a free flow prevention clam for use with the ambulatory pump of FIG. 1A.

FIG. 1A depicts an example ambulatory pump 100 and FIG. 1B depicts an example cassette 102 with free flow prevention for use with the ambulatory pump 100. The ambulatory pump 100 includes a receptacle 104 configured to receive the cassette 102. A peristaltic pump 106 within the receptacle 104 acts upon a tube 108 extending through a channel within the cassette 102 to pump fluid from a fluid container (e.g., a bag or a bottle; not shown) into a patient. An example free flow prevention clamp 110 is positioned within the cassette 102 to allow fluid flow through the tube 108 when the cassette is coupled to the ambulatory pump 100 within the receptacle 104 (during which time the peristaltic pump 106 controls fluid flow through the tube 108) and to selectively cut off fluid flow through the tube 108 when the cassette 102 is not coupled to the ambulatory pump 100 in order to prevent unintentional fluid flow through the tube (e.g., free flow).

The ambulatory pump 100 includes a user interface for interacting with the ambulatory pump 100. The illustrated user interface includes a display (which may be a touch-screen) and buttons 108. A user controls operation of the ambulatory pump via the user interface. The pump 100 additionally includes a housing for containing and supporting the components of the ambulatory pump 100 such as the peristaltic pump 106, electronics, and power supplies.

The free flow prevention clamp 110 includes a first elongate section 112a, a second elongate section 112b, and a clamping section 112c. The housing of the cassette 102 supports the free flow prevention clamp 110. The clamping section 112 is positioned within the cassette geometry such that, when the cassette 102 is received within the receptacle 104 of the ambulatory pump 100, the clamping section 112c extends across the channel receiving the tube 108. The housing of the cassette 102 may be rigid plastic or other material capable of supporting the tube 108 and free flow prevention clamp 110.

The first elongate section 112a extends from a first side of the clamping section 112c and along a first side of the cassette 102 parallel to the channel within the cassette 102 receiving the tube 108. The second elongate section 112b extends from a second side of the clamping section 112c and along a second side of the cassette 102 parallel to the channel receiving the tube 108. In the illustrated example, the free flow prevention clamp 110 is a staple-shaped leaf spring consisting of single piece of metal (e.g., spring steel). In other examples, the free flow prevention clamp 110 may be formed in pieces and/or of different materials (e.g., the elongate sections 112a, b may be metal and the clamping section 112c may be rigid plastic).

The ambulatory pump 100 also includes a pair of arc cams (a first arc cam 114a on one side of the receptacle is illustrated FIG. 1A, with the second hidden from view) for engaging the elongate sections 112a, b of the free flow prevention clamp in order to lift the clamping section 112c. Additionally, the ambulatory pump 100 includes a pair of wedge cams (a first wedge cam 116a on one side of the receptacle 104 is illustrated FIG. 1A, with the second hidden from view) for transitioning the free flow prevention clamp 110 from an open, manufactured/shipped state to an operational state, which is described in further detail below.

The cassette 102 also includes a first cutout 118a in a sidewall of the cassette 102 and a second cutout 118b in an opposite sidewall of the cassette 102. Additionally, the cassette 102 includes a touch pad 120 positioned on the first elongate section 112a adjacent a mid-point of the first elongate section 112a and the first cutout 118a. The touch pad 120 and cutout 118a facilitates engagement of the first elongate section 112a by a finger of an operator in order to manually lift the clamping section 112c to allow fluid flow through the tube 108 (e.g., for priming the cassette 102) when the cassette 102 is not received within the receptacle 104 of the ambulatory pump 100. The touch pad 120 may be a press fit piece of rigid plastic. Although the touch pad 120 is illustrated as only on the first elongate section 112a, a touch pad may also be provided on the second elongate section 112b. Additionally, the touch pad 120 may be omitted and an operator engage the elongate sections 112a, b directly to manually lift the clamping section 112c.

Figure 2A:
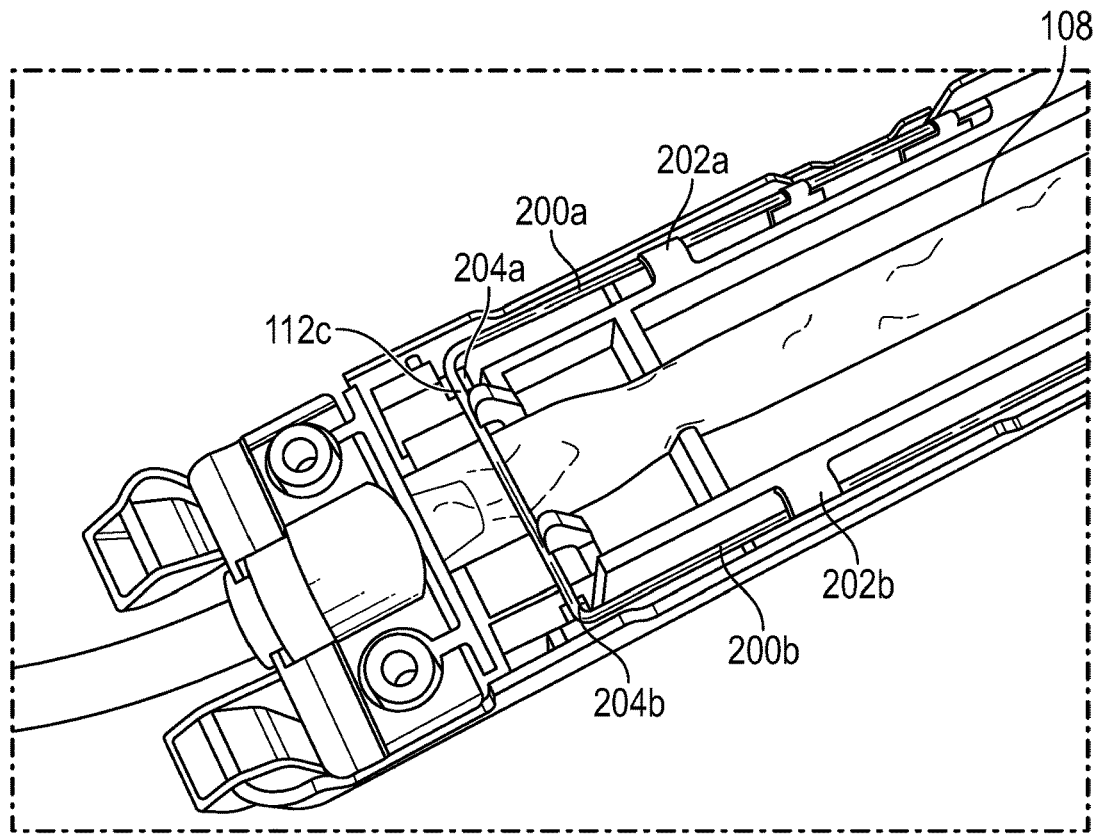
FIG. 2A is a partial perspective view of the cassette of FIG. 1B illustrating the free flow prevention clamp in an open, pre-operational state (e.g., shipped state).

FIG. 2A depicts the cassette 102 with the free flow prevention clamp 110 in an open, pre-operational state (e.g., manufactured/shipped state). The cassette 102 includes at first ledge 204a adjacent a first side of the clamping section 112c on one side of the channel receiving the tube 108 and a second ledge 204b adjacent a second side of the clamping section 112a on an opposite side of the channel receiving the tube 108. The ledges 204a, b support the clamping section 112c and oppose the downward force being applied to the clamping section 112c by the first and second elongate sections 112a, b. This prevents the clamping section 112c from occluding the tube 108 (e.g., for Ethylene Oxide, EtO, sterilization and/or priming) prior to insertion of the cassette 102 into the ambulatory pump 100.

The housing of the cassette 102 additionally includes a pair of override fulcrums 200a, b positioned below respective elongate sections 112a, b of the free flow prevention clamp 110 and a pair of occlusion fulcrums 202a, b positioned above respective elongate sections 112a, b of the free flow prevention clamp 110. The override fulcrums 200a, b are positioned between a midpoint of the first and second elongate sections 112a, b and the clamping section 112c. The occlusion fulcrums are positioned between the midpoint of the first and second elongate sections 112a, b and the override fulcrums 200a.

After the free flow prevention clamp 110 is moved off the ledges 204 and into an operational state, applying a force to the midpoints of the first and second elongate sections 112a, b (e.g., by the arc cams 114a, b upon attachment of the cassette 102 to the receptacle 104 of the ambulatory pump or by a user's finger) pivots the elongate sections a, b about the override fulcrums 200a, b to raise the clamping section 112c and allow fluid flow through the tube 108. Removing the force while in this state (e.g., by detaching the cassette or withdrawing the user's finger) shifts the pivot to the occlusion fulcrums 202a, b, which lowers the clamping section 112c and blocks fluid flow through the tube 108.

Figure 2B:
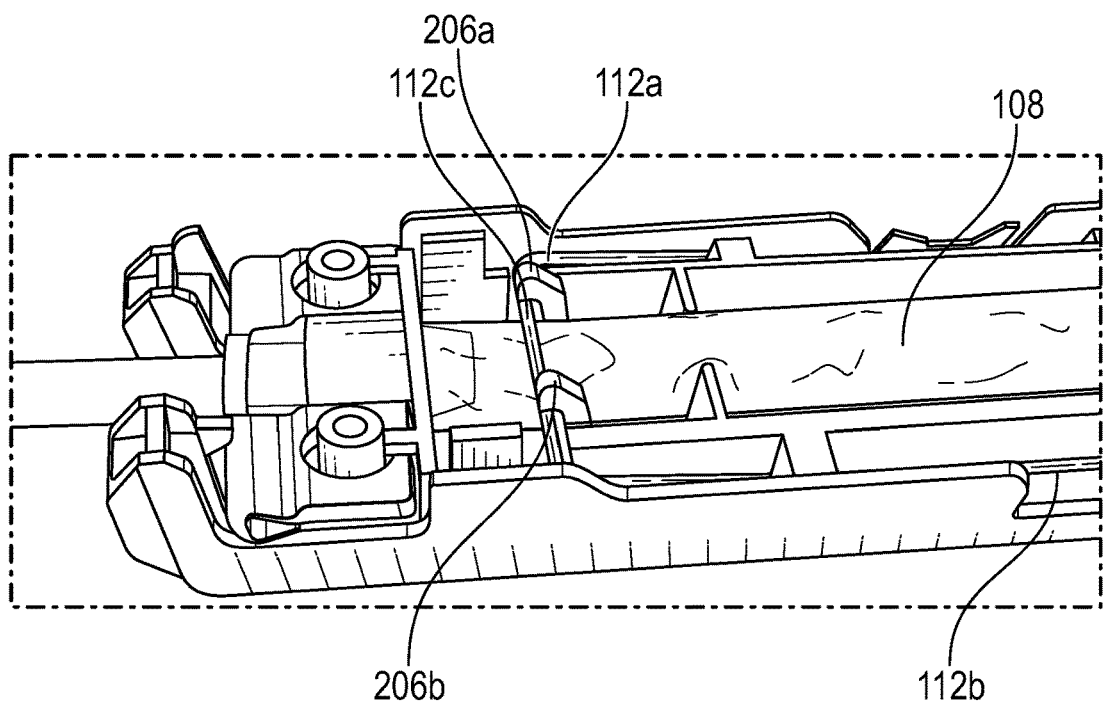
FIG. 2B is a partial perspective view of the cassette of FIG. 1B illustrating the free flow prevention clamp in a closed, post-operational state.
Figure 2C:
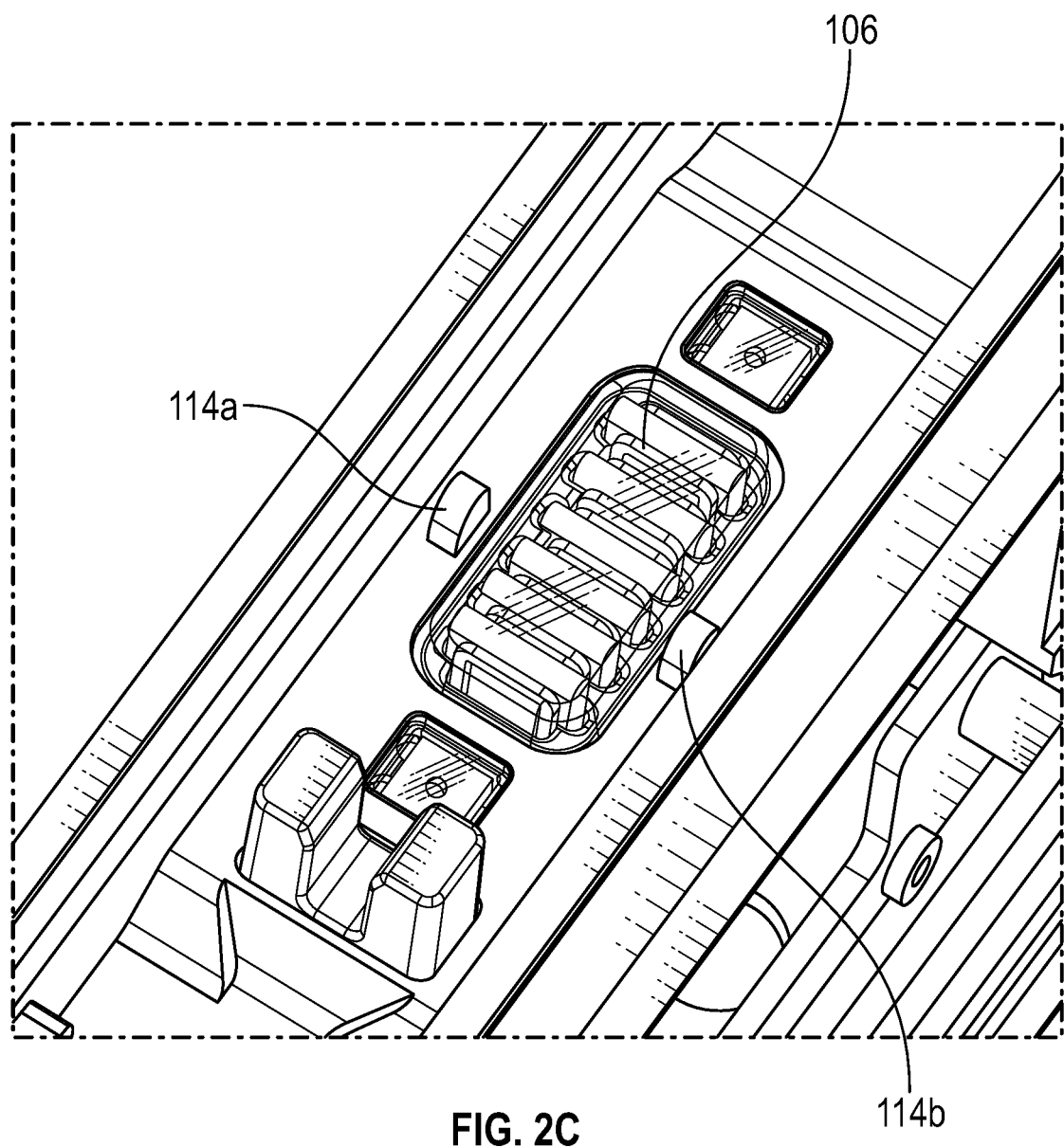
FIG. 2C is a partial perspective view of the pump of FIG. 1A illustrating arc cams that engage the free flow prevention clamp when the cassette is coupled to the pump.
Figure 2D:
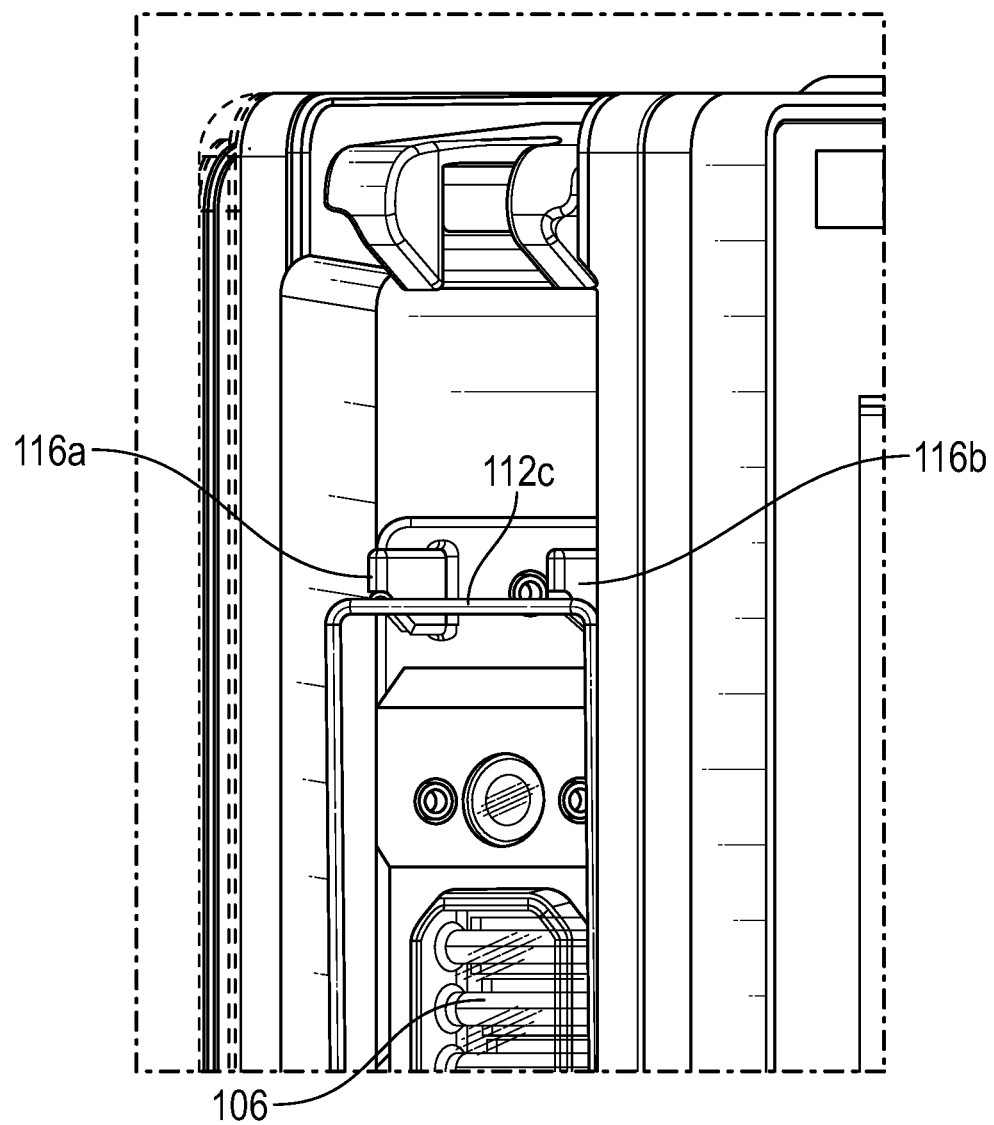
FIG. 2D is a partial perspective view of the pump of FIG. 1A illustrating wedge cams that engage the free flow prevention clamp to shift the free flow prevention clamp from a shipped state to an operational state when the cassette is coupled to the pump.

FIG. 2B depicts the cassette 102 with the free flow prevention clamp 110 in a closed, operational state and FIG. 2C depicts the arc cams 114 a, b and peristaltic pump 106 of the ambulatory pump 100. Guides 206a, b are provided to facilitate placement of the clamping section 112c of the free flow prevention clamp 110 onto the ledges 204, which maintains the tube 108 in an open condition. FIG. 2D depicts the wedge cams 116a, b and their relationship to the free flow prevention clamp when the cassette (not shown in FIG. 2D) is attached to the ambulatory pump 100.

The free flow prevention clamp 110 is moved off the ledges 204 and out of the open, pre-operational state by the wedge cams 116 as the cassette 102 is attached to the receptacle 104 of the ambulatory pump 100. To attach the cassette 102 to the receptacle 104, a user first inserts an end of the cassette 102 adjacent the clamping section 112c into the receptacle 104 near a bottom of the ambulatory pump 100. The user then rotates the cassette 102 downward about the toe-in into engagement with the ambulatory pump 100. As the cassette 102 is rotated into position, the arc cams 114 engage the elongate sections 112a, b to apply a force that raises the clamping section 112c and angled portions of the wedge cams 116 substantially simultaneously engage the clamping section 112c to shift the free flow prevention clamp 110 away from the ledges 204. In this manner, the tube 108 remains unobstructed by the clamping section 112c when the cassette 102 is attached to the ambulatory pump 100, allowing the peristaltic pump 106 to control fluid flow through the tube 108. In an example, once the free flow prevention clamp 110 is shifted from the shipped/pre-operational state into the operational state by the wedge cams 116, the free flow prevention clamp 110 remains in the operational state.

Removal of the cassette 102 from the receptacle 104 is accomplished by reversing the process. As the cassette 102 is rotated out of engagement with the ambulatory pump 100, the arc cams 114 disengage from the elongate sections 112a, b. With the force from the arc cams 114 removed, and the ledges 204 no longer positioned under the clamping section 112c due to the shift of the free flow clamp 110 during the insertion of the cassette 102, the clamping section 112 rotates downward about the occlusion fulcrums 202a to close off the tube 108 as depicted in FIG. 2B.

Figure 3A:
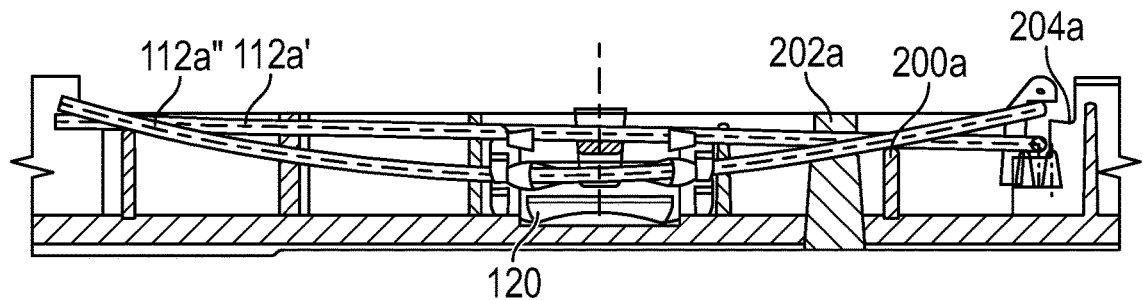
FIG. 3A is a partial side view of the example cassette of FIG. 1B depicting the free flow prevention clamp in an open condition and a closed condition.

FIG. 3A depicts movement of the first elongate section 112 after shifting the free flow prevention clamp 110 off the ledge 204a from the open, pre-operational state into the operational state. In the operational state, the first elongate section 112 can be in a closed condition (represented by first elongate section 112') or an open condition (represented by first elongate section 112"). In the closed condition, no force is applied to the midpoint of the first elongate section 112', resulting in the clamping section 112c rotating downward about the occlusion fulcrum 202a to close off the tube 108. In the open condition, force is applied to the midpoint of the first elongate section 112", resulting in the clamping section 112c rotating upward about the override fulcrum 200a to open the tube 108.

FIG. 3A additionally depicts movement of the touch pad 120 responsive to force applied at the midpoint of the first elongate section 112. In the absence of applied force, touch pad 120 is in a closed position that maintains clamping section 112c clamped against the tube 108. When force is applied (e.g., by an arc cam 114a or a user's finger), touch pad 120 is in an open position that raises clamping section 112c to permit fluid flow through the tube 108.

Figure 3B:
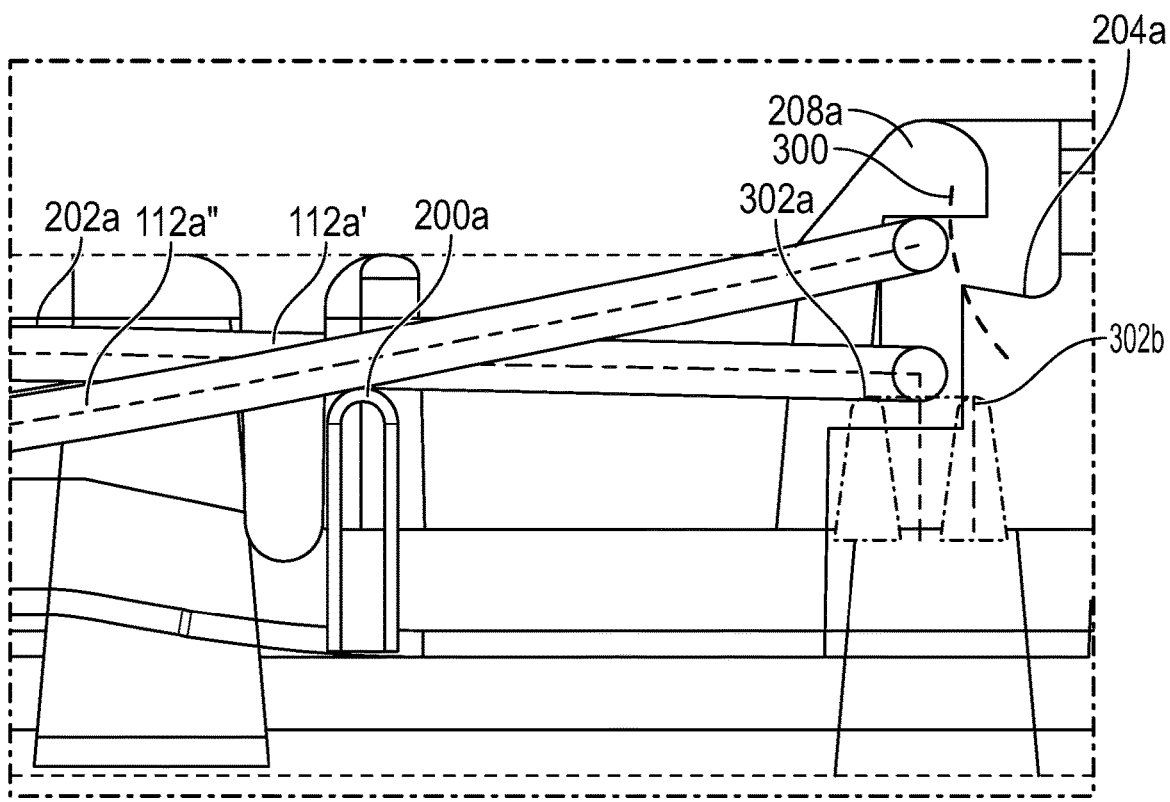
FIG. 3B is a partial side view of the example cassette of FIG. 1B illustrating features of the cassette for configuring the free flow prevention clamp in an open pre-operational state, an open operational state, and a closed post-operational state.

FIG. 3B depicts geometry of the housing of the cassette 102 supporting the free flow clamp 110. Shifting of the clamping section 112c of the free flow clamp 110 is represented by dashed wedge cam shift line 300. Occlusion fulcrum 202a acts on elongate section 112a' forcing clamping section 112c downward to occlude the tube 108. Occlusion ribs 302a and 302b are positioned perpendicular to the channel receiving the tube 108 and on either side of the clamping section 112c to assist with complete closure of the tube 108 when the clamping section 112c is in the closed condition. Override fulcrum 200a acts on elongate section 112a" forcing clamping section 112c upward to enable fluid flow through the tube 108.

Examples of the free flow prevention clamp 110 enable the cassette 102 to maintain the clamping section 112c in an un-occluded/open state prior to a first attachment of the cassette to the receptacle, maintain the clamping section in the un-occluded/open state upon the first attachment of the cassette to the receptacle, and transition the clamping section to an occluded/closed state upon detachment of the cassette from the receptacle. Additionally, examples of the free flow prevention clamp 110 enable the cassette to manually transition the clamping section to an un-occluded state after detachment of the cassette from the receptacle and/or transition the clamping section to the un-occluded state upon subsequent attachments of the cassette to the receptacle.

The terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as separately claimed subject matter.

While the foregoing has described what are considered to be the best mode and other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. An ambulatory pump system comprising:
    a cassette including a housing and a free flow prevention clamp,
    the free flow prevention clamp including a clamping section having a first side and a second side, a first elongate section extending from the first side, and a second elongate section extending from the second side, and the housing supporting the free flow prevention clamp and defining a channel for receiving a tube, the first elongate section and the second elongate section extending parallel to the channel and the clamping section extending across the channel,
        wherein the free flow prevention clamp is configurable within the housing in an open condition that allows fluid flow through the tube when force is applied to at least one of the first and second elongate sections and in a closed condition that prevents fluid flow through the tube when the force is removed from the at least one of the first and second elongate sections; and
    a pump body including a receptacle configured to receive the cassette, a peristaltic pump positioned adjacent the receptacle to act on the tube when the cassette is received by the receptacle, and at least one cam positioned within the receptacle to engage at least one of the first and second elongate sections to apply the force when the cassette is received by the receptacle, and
    wherein the cassette housing further includes at least one ledge adjacent the clamping section, the at least one ledge supports the clamping section in an open, pre-operational state, and the clamping section is moved off the at least one ledge when the cassette is received by the receptacle in the pump body.

2. An ambulatory pump system comprising:
    a cassette including a housing and a free flow prevention clamp, the free flow prevention clamp including a clamping section having a first side and a second side, a first elongate section extending from the first side, and a second elongate section extending from the second side, and the housing supporting the free flow prevention clamp and defining a channel for receiving a tube, the first elongate section and the second elongate section extending parallel to the channel and the clamping section extending across the channel, wherein the free flow prevention clamp is configurable within the housing in an open condition that allows fluid flow through the tube when force is applied to at least one of the first and second elongate sections and in a closed condition that prevents fluid flow through the tube when the force is removed from the at least one of the first and second elongate sections; and a pump body including a receptacle configured to receive the cassette, a peristaltic pump positioned adjacent the receptacle to act on the tube when the cassette is received by the receptacle, and at least one cam positioned within the receptacle to engage at least one of the first and second elongate sections to apply the force when the cassette is received by the receptacle, wherein the cassette housing includes a first side wall extending along a first side of the cassette adjacent the first elongate section and a second side wall extending along a second side of the cassette adjacent the second elongate section, at least one of the first and second side walls including an override cutout adjacent a midpoint of the respective elongate section for applying the force to configure the free flow prevention clamp in the open condition that allows fluid flow through the tube when the cassette is not received by the receptacle.

3. The ambulatory pump system of claim 2, wherein the cassette further comprises: a touch pad coupled to at least one of the first and second elongate sections adjacent the respective override cutout.

4. The ambulatory pump system of claim 1, wherein the cassette housing further includes an override fulcrum positioned between a midpoint of the first and second elongate sections and the clamping section.

5. An ambulatory pump system comprising:
a cassette including a housing and a free flow prevention clamp, the free flow prevention clamp including a clamping section having a first side and a second side, a first elongate section extending from the first side, and a second elongate section extending from the second side, and the housing supporting the free flow prevention clamp and defining a channel for receiving a tube, the first elongate section and the second elongate section extending parallel to the channel and the clamping section extending across the channel, wherein the free flow prevention clamp is configurable within the housing in an open condition that allows fluid flow through the tube when force is applied to at least one of the first and second elongate sections and in a closed condition that prevents fluid flow through the tube when the force is removed from the at least one of the first and second elongate sections; and a pump body including a receptacle configured to receive the cassette, a peristaltic pump positioned adjacent the receptacle to act on the tube when the cassette is received by the receptacle, and at least one cam positioned within the receptacle to engage at least one of the first and second elongate sections to apply the force when the cassette is received by the receptacle, wherein the cassette housing further includes an override fulcrum positioned between a midpoint of the first and second elongate sections and the clamping section and an occlusion fulcrum positioned between the midpoint and the override fulcrum.

6. The ambulatory pump system of claim 1, wherein the cassette is configured to perform the functions of:
maintaining the clamping section in an un-occluded state prior to a first attachment of the cassette to the receptacle;
maintaining the clamping section in the un-occluded state upon the first attachment of the cassette to the receptacle; and
transitioning the clamping section to an occluded state upon detachment of the cassette from the receptacle.

7. The ambulatory pump system of claim 6, wherein the cassette is further configured to perform the function of: manually transitioning the clamping section to an un-occluded state after detachment of the cassette from the receptacle.

8. The ambulatory pump system of claim 6, wherein the cassette is further configured to perform the function of: transitioning the clamping section to the un-occluded state upon subsequent attachments of the cassette to the receptacle.

9. The ambulatory pump system of claim 1, wherein the free flow prevention clamp is a staple shaped leaf spring.

10. A cassette comprising:
a free flow prevention clamp including a clamping section having a first side and a second side, a first elongate section extending from the first side, and a second elongate section extending from the second side, and
a housing supporting the free flow prevention clamp and defining a channel for receiving a tube, the first elongate section and the second elongate section extending parallel to the channel and the clamping section extending across the channel, wherein the free flow prevention clamp is configurable within the housing in an open condition that allows fluid flow through the tube when force is applied to at least one of the first and second elongate sections and in a closed condition that prevents fluid flow through the tube when the force is removed from the at least one of the first and second elongate sections, wherein the cassette housing further includes at least one ledge adjacent the clamping section, the at least one ledge supports the clamping section in an open, pre-operational state, and the clamping section is moved off the at least one ledge when the cassette is received by a receptacle of a pump body.

11. A cassette comprising:
a free flow prevention clamp including a clamping section having a first side and a second side, a first elongate section extending from the first side, and a second elongate section extending from the second side, and
a housing supporting the free flow prevention clamp and defining a channel for receiving a tube, the first elongate section and the second elongate section extending parallel to the channel and the clamping section extending across the channel, wherein the free flow prevention clamp is configurable within the housing in an open condition that allows fluid flow through the tube when force is applied to at least one of the first and second elongate sections and in a closed condition that prevents fluid flow through the tube when the force is removed from the at least one of the first and second elongate sections, wherein the cassette housing includes a first side wall extending along a first side of the cassette adjacent the first elongate section and a second side wall extending along a second side of the cassette adjacent the second elongate section, at least one of the first and second side walls including an override cutout adjacent a midpoint of the respective elongate section for applying the force to configure the free flow prevention clamp in the open condition that allows fluid flow through the tube when the cassette is not received by the receptacle.

12. The cassette of claim 11, wherein the cassette further comprises: a touch pad coupled to at least one of the first and second elongate sections adjacent the respective override cutout.

13. The cassette of claim 10, wherein the cassette housing further includes an override fulcrum positioned between a midpoint of the first and second elongate sections and the clamping section.

14. A cassette comprising:
- a free flow prevention clamp including a clamping section having a first side and a second side, a first elongate section extending from the first side, and a second elongate section extending from the second side, and
- a housing supporting the free flow prevention clamp and defining a channel for receiving a tube, the first elongate section and the second elongate section extending parallel to the channel and the clamping section extending across the channel, wherein the free flow prevention clamp is configurable within the housing in an open condition that allows fluid flow through the tube when force is applied to at least one of the first and second elongate sections and in a closed condition that prevents fluid flow through the tube when the force is removed from the at least one of the first and second elongate sections, wherein the cassette housing further includes an override fulcrum positioned between a midpoint of the first and second elongate sections and the clamping section and an occlusion fulcrum positioned between the midpoint and the override fulcrum.

15. The cassette of claim 10, wherein the cassette is configured to perform the functions of:
- maintaining the clamping section in an un-occluded state prior to a first attachment of the cassette to a receptacle of a pump body;
- maintaining the clamping section in the un-occluded state upon the first attachment of the cassette to the receptacle; and
- transitioning the clamping section to an occluded state upon detachment of the cassette from the receptacle.

16. The cassette of claim 15, wherein the cassette is further configured to perform the function of: manually transitioning the clamping section to an un-occluded state after detachment of the cassette from the receptacle.

17. The cassette of claim 15, wherein the cassette is further configured to perform the function of: transitioning the clamping section to the un-occluded state upon subsequent attachments of the cassette to the receptacle.

18. The cassette of claim 10, wherein the free flow prevention clamp is a staple shaped leaf spring.

\* \* \* \* \*